United States Patent
Hua et al.

(10) Patent No.: US 12,390,422 B2
(45) Date of Patent: Aug. 19, 2025

(54) TRANSDERMAL DRUG DELIVERY PATCH, DRUG DELIVERY SYSTEM AND DRUG DELIVERY

(71) Applicant: PASSPORT TECHNOLOGIES, INC., San Diego, CA (US)

(72) Inventors: Joe Hua, San Diego, CA (US); Masato Nishimura, Osaka (JP); Shohei Horie, San Diego, CA (US); Masahiro Mitsushima, Osaka (JP); Hirotoshi Adachi, San Diego, CA (US)

(73) Assignee: PASSPORT TECHNOLOGIES, INC., San Diego, CA (US)

( * ) Notice: Subject to any disclaimer, the term of this patent is extended or adjusted under 35 U.S.C. 154(b) by 752 days.

(21) Appl. No.: 17/623,171

(22) PCT Filed: Jun. 24, 2020

(86) PCT No.: PCT/US2020/039435
§ 371 (c)(1),
(2) Date: Dec. 27, 2021

(87) PCT Pub. No.: WO2020/264032
PCT Pub. Date: Dec. 30, 2020

(65) Prior Publication Data
US 2022/0339120 A1 Oct. 27, 2022

Related U.S. Application Data

(60) Provisional application No. 62/868,669, filed on Jun. 28, 2019.

(51) Int. Cl.
*A61K 9/70* (2006.01)
*A61K 9/00* (2006.01)
(Continued)

(52) U.S. Cl.
CPC .......... *A61K 9/7038* (2013.01); *A61K 9/0014* (2013.01); *A61K 31/422* (2013.01);
(Continued)

(58) Field of Classification Search
CPC .. A61K 9/7038; A61K 9/0014; A61K 31/422; A61K 31/485; A61K 31/702; A61K 38/26; A61K 47/22; A61K 47/26
See application file for complete search history.

(56) References Cited

U.S. PATENT DOCUMENTS

| 5,391,375 A | 2/1995 | Hille et al. |
| 6,922,578 B2 | 7/2005 | Eppstein et al. |

(Continued)

FOREIGN PATENT DOCUMENTS

| AU | 2014202524 A1 | 5/2014 |
| AU | 2016231468 A1 | 10/2016 |

(Continued)

OTHER PUBLICATIONS

Margetts et al., "Transdermal drug delivery: principles and opioid therapy," British Journal of Anaesthesia, 2007 (Year: 2007).*

(Continued)

*Primary Examiner* — Blessing M Fubara
(74) *Attorney, Agent, or Firm* — Knobbe, Martens, Olson & Bear, LLP

(57) ABSTRACT

To provide a transdermal drug delivery patch that can be suitably used for an immediate release application of a pharmaceutical with a comparatively low molecular weight. A transdermal drug delivery patch, provided with a matrix and at least one drug disposed within the matrix, wherein the matrix has a water holding capacity of 10 mg/cm$^2$ or less, and the drug is a pharmaceutical having a molecular weight of 5000 or less.

44 Claims, 5 Drawing Sheets

(51) Int. Cl.
*A61K 31/422* (2006.01)
*A61K 31/485* (2006.01)
*A61K 31/702* (2006.01)
*A61K 38/26* (2006.01)
*A61K 47/22* (2006.01)
*A61K 47/26* (2006.01)

(52) U.S. Cl.
CPC .......... *A61K 31/485* (2013.01); *A61K 31/702* (2013.01); *A61K 38/26* (2013.01); *A61K 47/22* (2013.01); *A61K 47/26* (2013.01)

(56) References Cited

U.S. PATENT DOCUMENTS

| | | |
|---|---|---|
| 7,141,034 B2 | 11/2006 | Eppstein et al. |
| 7,384,396 B2 | 6/2008 | Samuels et al. |
| 7,758,561 B2 | 7/2010 | Eppstein |
| 7,914,813 B2 | 3/2011 | Adachi et al. |
| 8,517,958 B2 | 8/2013 | Eppstein et al. |
| 8,641,689 B2 | 2/2014 | Messier et al. |
| 8,706,210 B2 | 4/2014 | Eppstein et al. |
| 9,486,616 B2 | 11/2016 | Eppstein et al. |
| 9,498,609 B2 | 11/2016 | Tagliaferri et al. |
| 9,579,380 B2 | 2/2017 | Eppstein |
| 9,918,665 B2 | 3/2018 | McRae et al. |
| 10,010,453 B2 | 7/2018 | Harima et al. |
| 10,166,378 B2 | 1/2019 | Tagliaferri et al. |
| 2004/0033254 A1 | 2/2004 | Song et al. |
| 2005/0181029 A1 | 8/2005 | Mitragotri et al. |
| 2007/0250018 A1 | 10/2007 | Adachi et al. |
| 2015/0110852 A1* | 4/2015 | Zhang ............... A61K 9/703 514/567 |
| 2018/0214917 A1 | 8/2018 | Valia |
| 2019/0110981 A1 | 4/2019 | Weimann |
| 2020/0023173 A1 | 1/2020 | Smith et al. |

FOREIGN PATENT DOCUMENTS

| | | | |
|---|---|---|---|
| EP | 3 311 762 B1 | 7/2020 | |
| EP | 3 411 110 B1 | 8/2020 | |
| JP | 2003-176465 A | 6/2003 | |
| JP | 2013-165686 A | 8/2013 | |
| WO | WO 2002/04570 A2 | 1/2002 | |
| WO | WO 2004/089347 A1 | 10/2004 | |
| WO | WO-2005046600 A2 * | 5/2005 | ............. A61K 47/08 |
| WO | WO 2013/169906 A1 | 11/2013 | |

OTHER PUBLICATIONS https://pubchem.ncbi.nlm.nih.gov/compound/tulobuterol, 2005 (Year: 2005).*
https://pubchem.ncbi.nlm.nih.gov/compound/sumatriptan), 2005 (Year: 2005).*
CB Bioparticles 2015 (Year: 2015).*
International Search Report and Written Opinion issued in application No. PCT/US2020/039435, dated Oct. 6, 2020.

* cited by examiner

TRANSDERMAL DRUG DELIVERY PATCH, DRUG DELIVERY SYSTEM AND DRUG DELIVERY

BACKGROUND OF THE INVENTION

Field of the Invention

The present invention relates to a transdermal drug delivery patch, a drug delivery system using this patch, and a drug delivery method. In particular, the present invention relates to a transdermal drug delivery patch, a drug delivery system and a drug delivery method that can be suitably used for an immediate release application of a pharmaceutical having a molecular weight of 5000 or less.

Description of the Related Art

Transdermal drug delivery systems have been marketed for various therapeutic indices over the past 30 years. Typically, transdermal drug delivery systems are devised as multilayer polymer laminates, in which a drug reservoir or drug polymer matrix creates two polymer layers: an occluded environment, which is interposed between an outer backing layer, which prevents drug loss through the backing surface, and an inner polymeric layer that acts as an adhesion and/or rate controlling membrane. In the case of the drug reservoir design, the reservoir is interposed between the backing and the rate controlling membrane. The drug is released only through the rate controlling membrane which may be microporous or nonporous. In a drug reservoir compartment, the drug may be in the form of a solution, a suspension or gel, or dispersed in a solid polymer matrix. The outer surface of the polymeric membrane is drug-compatible, and a thin layer of a hypoallergenic adhesive polymer may be applied.

In the case of the drug matrix design, there are two types: a drug-containing adhesive system and a matrix dispersion system. In a drug-containing adhesive system, the drug reservoir is formed by dispersing a drug in the adhesive polymer, developing a medicated polymeric adhesive by solvent casting, and melting the adhesive (in the case of a hot melt adhesive) into an impermeable backing layer. A non-medicated adhesive polymer layer may be applied to the top of the reservoir. In a matrix dispersion system, a drug is uniformly dispersed in a hydrophilic or lipophilic polymer matrix and fixed to the drug impermeable backing layer by solvent casting or extrusion. Instead of applying an adhesive to the surface of the drug reservoir, it is applied to form a peripheral adhesion.

JP 2006-509534 A discloses a transdermal delivery system for an active therapeutic agent from a dried pharmaceutical composition, wherein the system includes a device for easily carrying out transdermal delivery of an active therapeutic agent through the skin of a patient, and is capable of creating a patch wherein the device includes at least one microchannel on one region of the patient's skin, and at least one active therapeutic agent within the dried pharmaceutical composition. Furthermore, it is disclosed that the patch further includes a backing layer, an adhesive layer and a microporous liner layer, the dried pharmaceutical composition is a hydrophilic active therapeutic agent such as a protein, polypeptide, peptide, polynucleotide, oligonucleotide, growth factor, hormone, or the like, and further contains a stabilizer such as a disaccharide or the like.

JP 2013-512865 A discloses a transdermal treatment system (TTS) for administering a peptide to the patient on resected skin, wherein the transdermal treatment system includes a backing layer provided with a pressure sensitive adhesive layer containing at least one water insoluble polymer; an active ingredient layer containing at least one peptide and a carrier substance in the form of a sheet-like textile structure, and; a protective sheet.

JP 2008-543872 A discloses a device for inducing transdermal flow of a permeant into the patient via at least one formed pathway through the skin layer of a patient, wherein the device i) has a bottom surface, and includes a delivery reservoir including a non-biodegradable matrix defining a plurality of a conduit in the matrix, and ii) a non-soluble hydrophilic permeant disposed in at least a portion of the plurality of a conduit of the matrix. Furthermore, it is disclosed that the permeant includes a water-soluble filler such as a hygroscopic agent, or an anti-healing agent.

SUMMARY OF THE INVENTION

Problem to be Solved by the Invention

However, according to prior art it is not possible to obtain a transdermal drug delivery patch that can be suitably used for an immediate release application of a pharmaceutical with a comparatively low molecular weight, or more particularly, a pharmaceutical having a molecular weight of 5000 or less.

Means for Solving the Problem

The inventors of the present invention, after conducting diligent research, obtained the knowledge that it is possible to obtain a patch that can be suitably used for an immediate release application of a pharmaceutical having a molecular weight of 5000 or less that controls the rate of drug release by setting the water holding capacity of a matrix in which a drug is disposed, provided in a patch for transdermal drug delivery to a predetermined range.

Although not bound by any theory, it is believed that in the case where a drug is released into the body from a transdermal drug delivery patch applied to a biological membrane such as the skin, when a patch provided with a matrix in which a drug is disposed is applied to microporous skin, biological moisture such as a small amount of bodily fluid exudes from the body to the matrix through micropores, this biological fluid dissolves the drug disposed in the matrix, and the dissolved drug is transferred into the blood using a concentration gradient as the driving force. It is believed it is necessary for biological moisture of a predetermined amount or more to exude to the matrix to increase the release rate of the drug. On the other hand, depending on the composition and dose of the drug disposed in the matrix, there is a risk that exuded biological moisture will become excessive, leading to leakage from the patch and thereby yielding a reduction in the release rate of the drug due to a reduction in the concentration gradient. The present invention makes it possible to create a desirable item to control the release rate of a drug by adjusting the water retention capacity of the matrix in which the drug is disposed.

That is, the present invention is a transdermal drug delivery patch, provided with a matrix and at least one drug disposed within the matrix, wherein the matrix has a water holding capacity of 10 $mg/cm^2$ or less, and the drug is a pharmaceutical having a molecular weight of 5000 or less.

In the patch of the present invention, the foregoing matrix is preferably a non-woven fabric. Furthermore, the matrix preferably has a thickness of 100 µm or less. Moreover, the matrix preferably has a weight of 100 g/m² or less.

The foregoing pharmaceutical may have a molecular weight of 2000 or less. Furthermore, the pharmaceutical may be a non-peptide drug. Moreover, it is desirable that the pharmaceutical is administered at an amount of 0.1 to 30 mg.

The patch of the present invention may be further provided with at least one hygroscopic agent disposed within the matrix. The foregoing hygroscopic agent is preferably a saccharide. In the patch of the present invention, the total amount per unit area of the matrix with the drug and hygroscopic agent disposed within the matrix is preferably 0.1 to 30 mg/m². The total amount per unit area of the matrix with the drug and hygroscopic agent is more preferably 0.1 to 20 mg/m².

It is desirable that the patch of the present invention can withdraw subcutaneous fluid of an amount of 9.5 to 85 mg/cm² per unit area of the matrix. The patch of the present invention may be further provided with at least one additive disposed within the matrix. Furthermore, the patch of the present invention may be further provided with a backing layer for supporting the matrix. The patch of the present invention may be used to deliver a drug transdermally through one or more micropores formed by a porator.

The present invention, furthermore, is a system for delivering a drug through a subject biological membrane, provided with a porator and a patch, wherein the patch is provided with a matrix and at least one drug disposed within the matrix, wherein at least a portion of the drug is soluble in biological moisture received from the subject through the micropores formed by the porator, the matrix has a water holding capacity of 10 mg/cm², and the drug is a pharmaceutical having a molecular weight of 5000 or less.

In the system of the present invention, the foregoing porator may be at least one porator selected from a group composed of a heat porator, mechanical porator, laser porator, and water porator. The porator may be a thermally conductive element disposed so as to by in substantial physical contact with the biological membrane to deliver sufficient energy to thermally ablate the biological membrane. The porator may also be a thin layer tissue interface device.

The present invention, moreover, is a method for delivering a drug through a subject (however, excluding human) biological membrane, including a step for forming one or more micropores on a biological membrane, and a step for placing a patch so as to be in physical contact with the one or more micropores, wherein the patch is provided with a matrix and at least one drug disposed within the matrix, and at least a portion of the drug is soluble in biological moisture received from the subject through the one or more micropores, the matrix has a water holding capacity of 10 mg/cm², and the drug is a pharmaceutical having a molecular weight of 5000 or less.

DETAILED DESCRIPTION OF THE PREFERRED EMBODIMENT

Mode for Carrying Out the Invention

Figure 1:
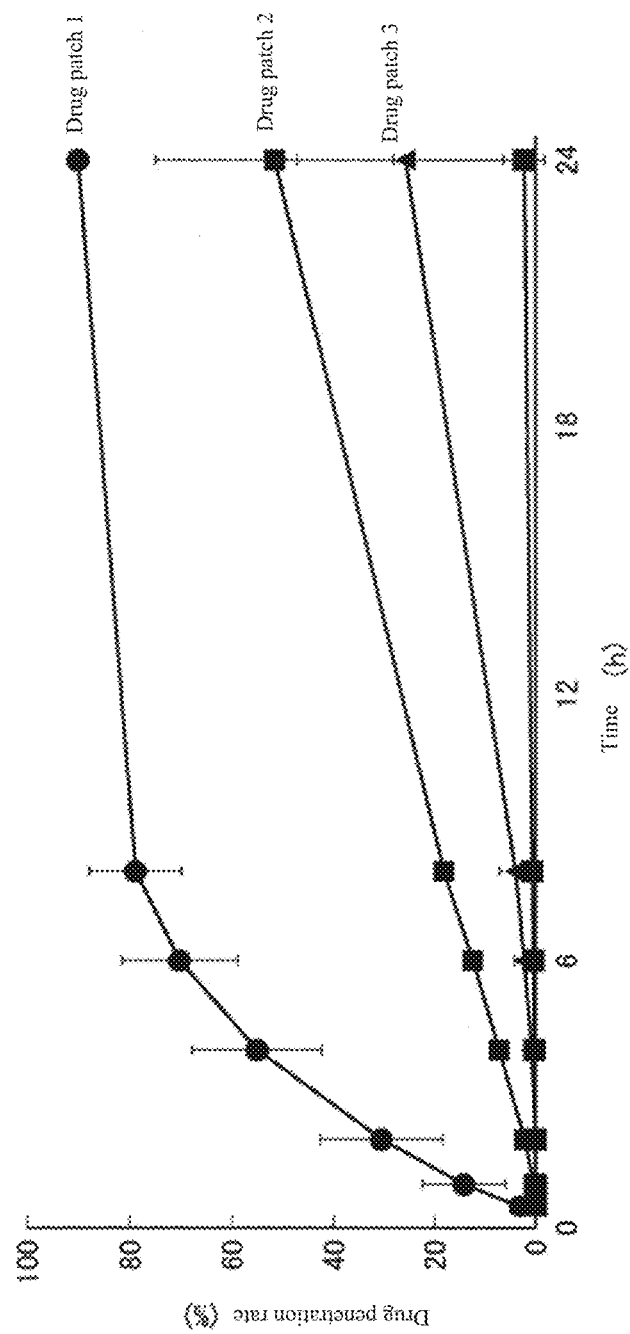
FIG. 1 is a drawing illustrating the drug release rate of drug patches created using matrices with a different water holding capacities.

When used in the present specification, the term "patch" may include a traditional drug reservoir or drug matrix patch, or any other type of patch that can be suitably used in transdermal drug delivery techniques in the non-limiting examples. In one embodiment of the drug reservoir design, the reservoir may be interposed between the backing and the rate controlling membrane. The drug is released only through the rate controlling membrane which may be microporous or nonporous. In the drug reservoir compartment, the drug may be in the form of a solution, a suspension or a gel, or dispersed in a solid polymer matrix. The outer surface of the polymeric membrane may be applied with a thin layer of a drug compatible hypoallergenic adhesive polymer. In one embodiment of the drug matrix design, it must always include both types of known drug-containing adhesive systems and matrix dispersion systems. In one embodiment of the drug-containing adhesive system, the drug reservoir may also be formed by dispersing a drug in the adhesive polymer, then spreading a medicated polymeric adhesive by solvent casting or melting the adhesive (hot melt adhesive) into an impermeable backing layer. A non-medicated adhesive polymer layer may be applied to the top of the reservoir. In one embodiment of the matrix dispersion system, a drug is uniformly dispersed on a hydrophilic or lipophilic polymer matrix and fixed to the drug impermeable backing layer. In another application, instead of applying an adhesive to the surface of the drug reservoir, it is applied to form a peripheral adhesion. All embodiments of patches that can be placed on the skin, including the foregoing traditional drug reservoir and drug matrix style patch, must be included as embodiments of the present invention.

When used in the present specification, "subcutaneous fluid" or "biological moisture" or "exudate" include but are not limited to water, plasma, blood, one or more proteins, interstitial fluid, skin tissue fluid, fluid from any layer of skin, sweat, serum, lymph fluid and/or combinations of two or more thereof. In one aspect, subcutaneous fluid according to the present invention is a water source including water.

When used in the present specification, "subject" refers to any organism having at least one biological membrane from which a subcutaneous fluid can be obtained. In one aspect, an exemplary biological membrane may be at least one skin layer from which a subcutaneous fluid can be obtained. For example, in one aspect, the subject is a plant. Or, in another aspect, the subject may be an animal. In one aspect, the animal may be a mammal. In an alternative aspect, the animal may be a non-mammal. Furthermore, the animal may be a cold-blooded animal, such as a fish, a reptile, or an amphibian. Or, the animal may be a warm-blooded animal, such as a human, livestock, livestock or even laboratory animals. Accordingly, it should be understood that the present invention is not limited to its use in the context of any particular subject or subject group.

When used in the present specification, "biological membrane" includes an inclusion layer or a separation layer that acts as a barrier within a cell or a barrier around a cell. In this aspect, it may be a lipid bilayer composed of lipid class molecules and randomly intertwined proteins. Furthermore, the biological membrane used in the present specification can prescribe an enclosed space or a compartment, and the cells therein can maintain a different chemical or biochemical environment than the environment outside the space or compartment. In this aspect, the biological membrane may be a selective permeable structure, and this determines whether the size, charge, and other chemical properties of the atoms and molecules that will attempt to pass through it can do so. In one aspect, the biological membrane may be a mucous membrane. Exemplary mucous membranes include, but are not limited to, oral, gum, gastrointestinal, neck, vaginal, rectal, intranasal, intraoral, and ocular membranes. In another aspect, the biological membrane may be a skin layer.

When used in the present specification, "skin layer" may be any one or more subject epithelium layers. For example, in one aspect, the skin layer includes the outermost layer of skin, that is, the stratum corneum. In an alternative aspect, the skin layer may include one or more layers of the epidermis below the stratum corneum, usually defined as the granular layer, spiny layer (Malpighian layer), and basal layer. It is recognized by those having skill in the art that there is essentially little to no resistance to transporting or absorbing a permeate through the epidermal layer beneath the stratum corneum. Accordingly, in one aspect of the present invention, at least one formed pathway in the subject skin layer is a pathway in the subject stratum corneum.

When used in the present specification, "additives" are also referred to as "enhancers," "chemical enhancers," "permeability enhancers," or "penetration enhancers," and the like: that is, it includes all additives that increase the fluidity of permeants, analytes, or other molecules through biological membranes or in tissue fluid. All cell envelope disordered compounds and solvents, as well as other chemical enhancers, are intended to be included. Moreover, pH adjusters, solubility adjusters (including ionic strength adjusters, salting-out agents, water soluble polymers), and fillers are intended to be included. In addition, all active force enhancers include, but are not limited to, acoustic energy of tissue, sonophoresis, iontophoresis, or electroporation, mechanical attraction, pressure, or local deformation. In some cases, hydrophilic penetration can also act simultaneously as a permeability enhancer (having a role as a permeant) or separately as a permeability enhancer. One or more enhancer techniques may be combined sequentially or simultaneously. For example, a chemical enhancer may be first applied to permeabilize the capillary wall, and then the iontophoresis or acoustic energy field may be applied to actively drive the permeant around the capillary bed and into the tissue including this.

When used in the present specification, "transdermal" or "transdermally" includes the passage of the permeant in one or more skin layers and through this to achieve effective therapeutic blood or local tissue levels of the permeant.

When used in the present specification. "formed opening," "artificial opening," or "micropore" means any physical pore of a biological membrane with a size suitable to deliver or eliminate fluid therethrough. Accordingly. "formed opening," "artificial opening," or "micropore" refers to the desired depth in a biological membrane, or small holes, openings or crevices made through a biological membrane. In one aspect, the term micropore refers to the result of any technology to be worn on the skin that yields a biological liquid product on the skin surface. In one aspect, an opening may be formed via the conduction of thermal energy taught in U.S. Pat. Nos. 5,885,211 and 7,141,034, or through mechanical processing, through explosives processing, or through frequency ablation. These teachings are incorporated in the present specification by reference. In this aspect, the size of holes or pores may have, for example, an approximate diameter of 1 to 1000, 5 to 700, 10 to 500, 50 to 300, 100 to 250, 50 to 100, or 70 to 90 microns. The holes or pores may be any shape, including, for example, cylinder, slit, hole, square, trough, crater, or the like. The term micropore is used in singular form for simplicity, yet it should be understood that the present device, system and method may form an array of a plurality of openings or holes.

When used in the present specification, "poration," "microporation," and any similar term means the shape of the outer layer of an organism for reducing small holes or gaps (hereinafter, to be called a "micropore") in or through tissue or biological membranes such as skin or mucous membranes or the like, or wall properties of this biological membrane for the passage of at least one permeant from one side of the biological membrane to the other for selected purposes. Preferably, holes or "micropores" formed in this way have an approximate diameter of 1 to 1000 microns, and are sufficiently spread across a biological membrane to break down the wall properties of the stratum corneum without adversely affecting the underlying tissue. In another embodiment, holes or micropores formed in this way have an approximate diameter of 1 to 1000, 5 to 700, 10 to 500, 50 to 300, 100 to 250, 50 to 100, or 70 to 90 microns. The term "micropore" is used in singular form for simplicity, yet it should be understood that the device of the present invention, may form a plurality of artificial openings. Poration reduces the wall properties of a biological membrane in the body for a selected purpose, or for certain medical or surgical purposes, and the microporation technique referred to in the present specification is mainly distinguished from openings formed by electroporation in that the typical smallest dimension of micropores which are usually at least about one micron or more in diameter and usually at least about one micron in depth, while openings formed by electroporation are typically only a few nanometers in any diameter. Nevertheless, electroporation is useful in facilitating the uptake of a selected permeant by a target tissue under the outer layer of an organism after the permeant has passed through micropores in these deeper tissue layers. For the purpose of the present application, "poration" and "microporation" are used interchangeably.

A "microporator" or "porator" is a component for a microporation device capable of microporation. An example of a microporator or porator includes, but is not limited to, a thermoporation device including a device having one or more filaments capable of conductively delivering thermal energy via direct contact with a biological membrane to cause an ablation of a membrane depth to an extent sufficient to form micropores: a heat transfer element disposed so as to be in substantial physical contact with a biological membrane to delivering sufficient energy to the biological membrane to thermally ablate the biological membrane; and, any heated, localized dye/absorbent layer: a mechanical ablation device including an electromechanical actuator, a micro lancet, and an array of solid or hollow micro needles or lancets; radio frequency ablation, acoustic energy ablation; a laser ablation system; a water pressure puncture device including a high pressure fluid jet puncture; a technique to be physically worn on the skin surface; or a skin ballistic delivery device or the like. The thin tissue interface described in U.S. Pat. No. 7,141,034, which is cited by reference in its entirety, is a further example of poration. When used in the present specification, "microporator" and "porator" are used interchangeably.

"Thin film layer interface" or "TFTI" are used to describe a device that creates micropores using thermal energy generated by the passage of a current via a resistive element, as well as methods of manufacturing and functionally operating TFTI devices. A TFTI device creates one or more micropores in a wide range of biological membranes. A TFTI has applications including analyte monitoring and thermal microporation of human skin for increasing the delivery of a permeate, including therapeutic agents, or tattoo pigments or the like. TFTIs are characterized by their ability to rapidly and efficiently create a pattern or array of micropores on the surface of a biological membrane. This pattern can be any geometric space of micropores with various possible pore densities. In one aspect, the pore density is as high as one pore every 0.2 mm$^2$, pore density covers an entire porated area ranging from a few square millimeters to several hundred equilibrium centimeters, and includes 0.005 to 800, 0.01 to 500, 0.1 to 500, 1 to 300, 10 to 200, 25 to 100, and 50 to 75 square centimeters. TFTI devices are designed to be thin, flexible conforming structures that may form an interface between a biological membrane and a controller. Or, TFTIs may be integrated with the controller itself, and this integrated device may be in contact with the biological membrane. The controller portion is not limited to other active components such as each poration element or electrode or piezoelectric transducer or the like, and is supplied to a TFTI using an electrical signal required to affect other functions such as the TFTI's poration, or the TFTI's iontophoresis, sonophoresis, electroporation, or impedance measurement of contact tissue. TFTIs may be flexible and adaptable to the shape of the target biological membrane. TFTIs are very thin, may be processed for weighing, used separately from a patch, or in an integrated form, and are also connected to the controller or power source through an umbilical cable that permits a familiar form to many users. When one or more active additional flux enhancement features that can be controlled are incorporated into a TFTI, such as, but not limited to, pressure regulation, mechanical manipulation, iontophoresis, electroosmosis, sonophoresis or electroporation, activation of this additional flux enhancement feature can be controlled by a remote controller module either in a preprogrammed manner, in a user controlled manner via input to the controller, or in an automatic closed loop manner. Here, the infusion rate of the permeate is adjusted as a function of the measured level of the selected analyte in vivo, or another measurable property of an organism. Other identifiable characteristics can include heart rate, blood pressure, temperature, respiration, and skin surface conductivity. For example, in one embodiment, it is useful to control the rate of insulin infusion based on real time measurements of glucose concentration in interstitial fluid or serum of an organism. In another embodiment, it is desirable to use several therapeutic compounds, and more particularly, compounds that have a narrower therapeutic window to identify when effective drug levels become so bad that the negative side effects on something are extremely unbearable in order to adjust the infusion rate based on measurable levels of this compound in vivo so as to be extremely accurate, thus enabling a very accurate, self-applicable method to achieve and maintain drug concentrations within a desired therapeutic window, regardless of the patient's weight or metabolism. In the design and manufacture of TFTIs, many conductive traces including TFTIs can be used to fulfil multiple functions. For example, a trace used to deliver a short pulse current to a resistance poration element that induces thermal cycling can also be used for closed loop feedback control of microporation, or to incorporate an enhancement as an electrode for iontophoresis or electroporation treatment, and this is implemented after micropores have been formed.

When used in the present specification, "iontophoresis" refers to applying an external electric field to the tissue surface through delivery of an ionized or non-ionized form of a drug delivered together with the use of two or more electrodes, as well as water flow associated with ion transport (electroosmosis) to a tissue or biological fluid or similar extract of an analyte.

When used in the present specification, "electroporation" refers to creation through an electric current in openings in cell walls that are of a much smaller order than micropores. Openings formed by electroporation are typically only a few nanometers in any dimension, for example, 1 to 10 nanometers. In one embodiment, electroporation is useful for promoting cellular uptake of permeants selected according to target tissue beneath the outer layer of the organism after the permeate has passed through micropores into deeper layers of tissue.

When used in the present specification, "sonophoresis" or "sonification" refer to piezoelectric crystals, or acoustic energy that may contain vibrations commonly described as ultrasound, caused by oscillating other electrochemical elements by passing an alternating current through a material. The use of acoustic energy to enhance the permeability of skin to drug molecules is called sonophoresis or phonophoresis.

When used in the present specification, "bioavailability" refers to absolute bioavailability and relative bioavailability. Absolute bioavailability determines the proportion of an active drug in systemic circulation after a drug has been non-intravenously administered (oral, rectal, transdermal, subcutaneous, etc.). In pharmacokinetics, it is necessary to obtain changes in plasma drug concentration per unit time in both intravenous administration (IV) and non-intravenous administration to determine the absolute bioavailability of a drug. Absolute bioavailability is determined by dividing the area under concentration curve (AUC) calculated when a fixed amount of a drug has been non-intravenously administered by the AUC calculated when intravenously administered (IV) with the same amount. Furthermore, relative bioavailability is used to evaluate differences in absorbability thereof in different routes of administration, therefore if the control route of administration is intravenous, the value thereof is the absolute bioavailability. Furthermore, relative bioavailability is used when comparing absorbability of a certain drug with absorbability of a control drug. For example, in a generic drug, relative bioavailability in which a targeted generic drug is the control drug is used to evaluate bioequivalence.

The transdermal drug delivery patch according to the present invention is provided with a matrix and at least one drug disposed within the matrix, wherein the matrix has a water holding capacity of 10 mg/cm$^2$ or less, and the drug is a pharmaceutical having a molecular weight of 5000 or less.

The matrix used in the present invention has a water holding capacity of 10 mg/cm$^2$ or less. The water holding capacity of the matrix means the amount of moisture the matrix can hold per 1 cm$^2$. Specifically, a 1 cm$^2$ matrix is prepared, and this is immersed in a solution (phosphate buffered saline containing 0.1% surfactant (Tween 80)) for a sufficiently long amount of time. Following this, the matrix is slowly pulled out of the solution for around five seconds, the weight of the sample before immersion measured in advance is subtracted from the weight of the sample holding the liquid, and then it is possible to determine the water holding capacity of the matrix per unit area (1 cm$^2$). The matrix used in the present invention preferably has a water holding capacity of 10 mg/cm$^2$ or less, and more preferably has a water holding capacity of 1 mg/cm$^2$ to 10 mg/cm$^2$.

Although the structure of the matrix used in the present invention is not particularly limited, a non-woven fabric is preferable. Non-woven fabrics made of hydrophobic material (polyester, polypropylene, polysulfone, EVAL, polyacrylonitrile, cellulose, nylon, or the like), and non-woven fabrics made of hydrophilic material (cellulose, wool, silk, rayon, cupra, pulp, or the like), or the like are given as examples of preferable non-woven fabrics. In addition to non-woven fabrics, the matrix used in the present invention may take the form of mesh, woven fabric, paper, or the like. Additionally, the matrix used in the present invention may also take the form of film. In this case, it is best to roughen the film surface to make it uneven as it is difficult to support the drug when the film surface is too smooth. Furthermore, the matrix used in the present invention may also take the form of a membrane. If a hydrophobic membrane is used, there is no penetration of pores, giving a film-like feeling of use. On the other hand, if a hydrophilic membrane is used, penetration into the inner part becomes easy, giving a nonwoven fabric-like feeling of use. It is desirable to use a membrane with low density, from the viewpoint of the drug amount and water amount that can be supported by the inner part. The water holding capacity of the matrix may be controlled by adjusting the thickness and weight of the matrix. It is preferable that the matrix has a thickness of 100 μm or less. Moreover, the matrix preferably has a weight of 100 g/m$^2$ or less.

The matrix used in the present invention has a surface adapted so as to be in contact with the biological membrane, and furthermore, is adapted so as to absorb or otherwise receive biological moisture from at least one pathway formed through the biological membrane, and in this case the patch is disposed so as to be in fluid communication with at least one path formed. The matrix may include at least one polymer, and may include two or more polymers. The polymer (single or a plurality) may be a water soluble or water insoluble polymer. A single matrix may include both a water soluble polymer and a water insoluble polymer. Polyethylene glycol (PEG, PEO, or POE), polyvinyl alcohol (PVA or PVOH), and polyvinyl pyrrolidone (PVP) are given as non-limiting examples of a water soluble polymer. Ethylene vinyl acetate (EVA) and ethyl cellulose (EC) are given as non-limiting examples of a water insoluble polymer. The matrix material, in terms of non-limiting examples, accounts for approximately 1% by weight to approximately 99% by weight of the patch, and furthermore, accounts for an additional amount of approximately 25% by weight, approximately 30% by weight, approximately 35% by weight, approximately 40% by weight, approximately 45% by weight, approximately 50% by weight, approximately 55% by weight, approximately 60% by weight, approximately 65% by weight, approximately 70% by weight, approximately 75% by weight, and approximately 80% by weight of the patch. Moreover, the matrix material may also account for any amount of weight percentage in any range derived from these values. For example, in terms of non-limiting examples, the matrix material may be in the range of approximately 1 to approximately 60% by weight of the patch, approximately 20 to approximately 60% by weight of the patch, approximately 20 to approximately 40% by weight of the patch, and a further approximately 1 to approximately 40% by weight of the patch.

The matrix material may include a combination of a water-insoluble polymer material or polymer material. For example, although not limited, in one aspect, the matrix includes ethylene vinyl acetate (EVA) copolymer, ethyl cellulose (EC), polyethylene, ethyl polyacrylate, copolymer of ethylene and ethyl acrylate, and any combination thereof. In one aspect, the matrix may include ethylene vinyl acetate copolymer having a relative percentage of vinyl acetate in the range of 0% to approximately 60%, and may contain a percentage of an additional vinyl acetate, such as approximately 0%, 1%, 5%, 10%, 15%, 20%, 25%, 30%, 35%, 40%, 45%, 50%, 55%, and 60% and the like, and any percentage of a range derived from these values. Note that in another aspect, the ethylene-vinyl acetate copolymer contains approximately 40% vinyl acetate.

The drug used in the present invention is a pharmaceutical having a molecular weight of 5000 or less. Examples of the drug generally include, but are not limited to, anti-infective agents, such as antibiotics and antiviral agents; analgesics and analgesic combinations; anorectic agents; anthelmintics; anti-arthritic agents: anti-asthma agents; anticonvulsants; antidepressants: antidiabetic drugs; antidiarrheals; antihistamines; anti-inflammatory drugs: antimigraine preparations; antiemetic agents: antineoplastic agents: anti-angiogenic agents; Parkinson's disease treatments; antipruritics; antipsychotic drugs; antipyretics; anticonvulsant drugs: anticholinergic drugs; sympathomimetic drugs; and xanthine derivatives: cardiovascular agents, such as potassium and calcium channel blockers; beta blockers, alpha blockers, and antiarrhythmic agents; antihypertensives; and diuretics and antidiuretics: vasodilators, commonly for the coronary artery, the periphery, and the brain; central nervous system stimulants; and vasoconstrictors: cough and cold preparations, such as decongestants; hormones, such as estradiols and other steroids, such as corticosteroids; sleep medication; immunosuppressants: muscle relaxants: parasympatholytics; psychostimulants; sedatives; tranquilizers; antifibromyalgia drugs; xerostomia drugs; bone resorption inhibitors: agents that build bone strength: agents that reduce bone fragility; anti-incontinence agents: anti-anxiety agents; antihypertrophic agents; anti-edema agents: anti-obesity drugs; bone resorption inhibitors: anesthetics; anxiolytics; sedatives; muscle relaxants; acetylcholinesterase inhibitors; ACE inhibitors; anticoagulants; sleeping medication; anti-compulsive agents; anti-bulimia drugs; antiemetics; anti-anxiety agents; NSAIDs; antirheumatic agents; hypothyroid drug treatments; hypothyroid drug treatment NMDA receptor antagonists; NMDA receptor agonists; partial NMDA receptor agonists; ADHD treatment drugs, antispasmodic drugs, antispasmodic agents, migraine preventive drug; benign prostate hypertrophy drug; sedatives; anesthetics; pulmonary arterial blood pressure lowering agents; sleep medication; osteoporosis drugs; anti-inflammatory drugs; diabetic glycemic control agents; multiple sclerosis drugs; thrombocytopenia drugs; and myeloid reconstitution drugs.

Specific examples of the pharmaceutical may include acitretin (Soriatane), amitriptyline (Elavil), alendronate sodium, aripiprazole (Abilify), bethanechol HCl (Urecholine), bromocriptine (Parlodel), bumetanide (Bumex), bupivacaine (Marcaine), buprenorphine (Buprenex), buspirone (BuSpar), cetirizine HCl, citalopram (Celexa), clorazepate (Tranxene), clomipramine HCl, cyclobenzaprine (Flexeril), donepezil (Aricept), doxazosin (Cardura), enalapril (Vasotec), enoxaparin (Lovenox), escitalopram (Lexapro), felodipine (Plendil), fentanyl (Sublimaze, Duragesic), Fosinopril, galantamine HBr (Reminyl, Razadyne ER), glyburide (Glucotrol), granisetron (Kytril), haloperidol (Haldol), hydrocodone hydrogen tartrate, hydrocortisone acetate, hydroxyzine HCl, isradipine (DynaCirc), ketorolac (Acura, Toradol), leflunomide (Arava), levothyroxine (Levoxyl, Levothroid. Synthroid), lisinopril (Prinivil, Zestril), lorazepam (Achiban), loxapine (Loxitane), meloxicam (Mobic), memantine (Namenda), methylphenidate (Ritalin, Concerta), methimazole (Tapazole), metoclobramide (Reglan), metolazone (Mykrox, Zaroxolyn), Mirtazapine (Remeron), montelukast, nalbuphine (Nubain), neostigmine (Prostigmin), nortriptyline HCL, olanzapine (Zyprexa), ondansetron (Zofran), oxybutynin chloride (Ditropan Chlorinated Oxybutynin (Ditropane XL), oxycodone HCL, oxymorphone (Numorphan), palonosetron (Aloxi), paliperidone, paliperidone palmitate, paroxetine (Paxil), pergolide (Permax), perphenazine (Trilafon), phenytoin sodium, pramipexole (Mirapex), prochlorperazine (Compazine), procyclidine (Kemadrin), promethazine HCl, propranolol HCl, protriptyline (Vivactil), ramipril, risperidone (Risperdal), ropinirole (Requip), rosiglitazone (Avandia), selegiline (Eldepryl) (R-(−) 1 deprenyl hydrochloride), tamsulosin (Flomax), temazepam (Restoril), thiethylperazine (Torecan), tiagabine (Gabitril), timolol, tramadol, treprostinil sodium (Remodulin), tropisetron (Navoban), warfarin sodium, ATI5923, zolpidem tartrate, and DPP-4 inhibitors (sitagliptin (Januvia), vildagliptin (Galvus), saxagliptin (BMS477118), alogliptin (SYR-322), denagliptin (Redona), PHX1149, TA-6666, GRC8200/EMD675992, MP513, PSN9301, R1579, B11356, PF-734200, ALS2-0426, TS-021, AMG221, ABT-279, SK-0403, KRP-104, SSR162369, ARI2243, S40010, PT-630, SYR-619, E3024, and A-899301).

The drug used in the present invention may be a therapeutic agent conventionally known for injection administration. Specific examples of such as therapeutic agent include adenosine, fluorouracil, alprostadil, amikacin sulfate, amiodarone, azithromycin, bleomycin, carboplatin, ceftriaxone, ciprofloxacin, cisplatin, dacarbazine, daunorubicin HCl, deferoxamine mesylate, desmopressin acetate, dexamethasone sodium phosphate, dipyridamole, doxorubicin HCl, enalaprilat, epirubicin HCl, fluconazole, fludarabine phosphate, flumazenil, phosphenytoin sodium, granisetron HCl, haloperidol decanoate, aloperidol, idarubicin HCl, ifosfamide, irinotecan HCL, L-cysteine HCl, leucovorin calcium, leuprolide acetate, medroxyprogesterone acetate, mesna, methylprednisolone acetate, metoclopramide, mitoxantrone, norepinephrine tartrate, octreotide acetate, ondansetron, ONXOL (registered trademark) (paclitaxel), oxycin, pamidronate disodium, pancuronium bromide, promethazine HCl, propofol, sulfamethoxazole and trimethoprim, terbutaline sulfate, testosterone cypionate, tobramycin, TOPOSAR (registered trademark) (etoposide), vecuronium bromide, VINCASAR PFS (registered trademark) (vincristine sulfate), vinorelbine tartrate, ZANOSAR (registered trademark) (streptozotocin), Abraxin, Actrel, Adensocan, Alimta. Amevive, Amikacin, Anzemet. Arimidex, Arixtra, Aromasin, Avastin, Aponex, Betaseron, Bicnu, Botox, Campus, Camptosar, Casodex. Ceenu. Cerezyme, Cetrozide, Copaxone. Copegas. Cytoxan, Depo-testosterone, Dobutamine, Doxil, Eligard, Eloxatin, Elspar, Enbrel, Erbitux, Ettilol, Fabrazyme, Faslodex, Follistim, Fuzeon, Ganirex (Antagon), Gemzar, Genotropin, Genotropin Miniquick, Gleevec, Gonal-f, Herceptin, Hexarene, HumatroPen, Humira, Hycamtin, Infergen, Infumorph, Intron A, Kineret, Kuvan, triol-Intra. Lucentis, Rubron Pediatric, Macugen, Matsuran, Menopur, Mastergen, Myobloc, Nabi-HB, Neumega, Neupogen, Nexavar, Norditropin, Nutropin, Nutropin AQ, Orencia, Ovidrel, Pegasys, Pegintron, Pantam, Prograf, Proleukin, Pulmozyme, Rebetol, Rebif. Reclast, Refludan, Remicade, Repronex. Revlimid, RibaPak, Ribavirin, Rispadal Consta, Rituxan, Roferon-A, Saizen, Sandostatin LAR, Therostim, Sprycel, Sapprelin LA, Sutent, Synagis, Synthroid, Tarceva. Tasigna, Tamoxifen, Taxotere, Temodar, Tev-Tropin, Thalidomide, Thyrogen, Tobi, Tubersol, Tysabri, Tykerb, Velcade. Vesanoid, Vidaza, Vinblastine. Vincristine, Viread. Vistide, Vitamin K, Vivitrol, Xeloda, Zometa, Advate, AlphaNight, AlphaNin, Aranesp, Bebulin, Benefix, Epogen, Forteo. Fragmin, Helixate, Hemofil, Humate, Hyate, Koate, Kogenate, Leukine. Lovenox, Monoclate, Mononine. Myocristin, Neulasta, Neumega, Novarel, NovoSeven, Procrit, Profilin, Raptiva, Revetron, Recombinate, Refacto, Caverject, D.H.E. 45, Zofran, BayRho D, Protropin, Delatestryl, Plenaxis, Hemofil-M, Monarch-M, Proplex T, Hyalgan. Schwarz, Synvisc, Excellence, Zoladex, Pergonal, Carimune, Gamimune N, Gammagard, Gammar, Iveegam, Panglobulin, Polygam, and Venoglobulin.

The foregoing pharmaceutical may have a molecular weight of 2000 or less, so as to contain a so-called medium weight molecule drug and a low weight molecule drug, may further have a molecular weight of 700 or less, so as to contain a so-called low molecular weight drug, and ideally may have a molecular weight of 500 or less. Furthermore, the pharmaceutical may be a non-peptide drug. Moreover, it is desirable that the pharmaceutical is administered at an amount of 0.1 to 30 mg per 1 $cm^2$ of the matrix.

The patch of the present invention may be further provided with at least one hygroscopic agent disposed within the matrix. The hygroscopic agent may be a water-soluble substance, a mixture in a water-soluble state or the like, and is preferably a substance having high water solubility. The foregoing hygroscopic agent is preferably a saccharide. Note that if the drug is a substance soluble in an exudate or is in a soluble state, the drug may also be regarded as a hygroscopic component. In the patch of the present invention, the total amount per unit area of the matrix with the drug and hygroscopic agent disposed within the matrix is preferably 0.1 to 30 $mg/m^2$. The total amount per unit area of the matrix with the drug and hygroscopic agent is more preferably 0.1 to 20 $mg/m^2$. In addition to the drug and hygroscopic agent, the patch of the present invention may also be provided with any component disposed within the matrix and that dissolves in an exudate, for example, an excipient, stabilizer, pH adjuster, buffer, preservative, antiseptic, solubility enhancer, thickener, antioxidant, transdermal absorption enhancer, irritation modifier, chelating agent, or the like. The patch of the present invention may further be provided with water, alcohol, an organic solvent, and a mixture of these or the like.

It is desirable that the patch of the present invention can withdraw subcutaneous fluid of an amount of 9.5 to 85 $mg/cm^2$ per unit area of the matrix. The patch of the present invention may be further provided with at least one additive disposed within the matrix. Furthermore, the patch of the present invention may be further provided with a backing layer for supporting the matrix. A support coated with an acrylic, rubber or silicone adhesive may be used as a preferred backing layer. The support in this case is not particularly limited as long as it is suitable for supporting a matrix provided with a drug, and a stretchable or non-stretchable one may be used. Specifically, polyethylene, polypropylene, polybutadiene, ethylene vinyl acetate copolymer, polyvinyl chloride, polyester, and nylon. A film or sheet such as polyurethane or the like, a laminated body of these, a porous body, foam, cloth and non-woven fabric, as well as a laminate product of these or the like may be used. The patch of the present invention may be provided with a release coating, which peels off prior to application to the skin, on the surface of the patch, or on the surface of an adhesive provided on backing layer support. Polyethylene, polypropylene, polyester, polyethylene terephthalate, and those obtained by release-treating these with silicone, or a release paper or the like may be used as such a release coating. The patch of the present invention may be used to deliver a drug transdermally through one or more micropores formed by a porator. The porator and the patch may be independent of each other, or they may be combined. In the case where the porator and patch are used in combination, the patch is adhered while aligning it with an area of skin that has been heat-pierced using a porator. During this, it may be aligned by sight, or a system for aligning it may also be used.

The patch of the present invention, in a system for delivering a drug through a target biological membrane, may be used together with the porator by ensuring that at least a portion of the drug is soluble in biological moisture received from the target through the micropores created by the porator.

The patch of the present invention can also be used in a method for delivering a drug through a target biological membrane, wherein the method includes a step for forming one or more micropores on a biological membrane, and a step for placing a patch so as to be in physical contact with the one or more micropores, by making sure that at least a portion of the drug is soluble in biological moisture received from the target through the one or more micropores.

The patch of the present invention may be prepared according to the following method. First, a punching die is used to form a backing layer material into a predetermined size (for example, a 25×25 mm square). Next, a punching die is used to form a matrix material (for example, a non-woven fabric) into a predetermined size (for example, a 10×10 mm square). The formed matrix material is affixed to the center part of the backing layer material (hereinafter called a blank patch). An additive (ascorbic acid, sucrose, citric acid monohydrate or the like) and the drug are weighed, then a solution is added (deionized water, PBS, alcohol or the like), stirred until completely dissolved, thereby preparing a drug solution. A mechanical pipette is used to drip a desired drug solution onto the matrix material area of the blank patch. It is dried in a 60° C. oven for 20 to 50 minutes, then the patch structure is obtained. A release coating (release liner) is coated on this patch structure. The completed patch is made into a pouch together with a drying agent by sealing with a heat sealer.

The patch of the present invention may be used according to the following method. The patch of the present invention is particularly expected to be applied to diseases where an immediate effect is expected, and diseases that require a PK profile comparable to subcutaneous injection. Oral drug administration is generally where a drug is absorbed mainly from the intestinal tract, and it takes time for the drug to reach the intestinal tract. On the other hand, when the patch of the present invention is used to deliver a drug transdermally through one or more micropores formed by a porator, by perforating the outermost stratum corneum of the epidermis and applying a patch there, the drug passes through the epidermis, diffuses into the capillary dermis and enters systemic circulation. Thus, the patch of the present invention may provide drug administration means to replace injections, which can be suitably used for immediate release applications of drugs, and is sufficiently faster than oral drug administration.

EXAMPLES

Examples will be described in detail according to the present invention below, yet the present invention is not limited to such examples.

Measurement Method of Water Holding Capacity

Tween 80 (Spectrum Chemical Mfg. Corp. or Croda), which had been weighed, was dissolved in phosphate buffered saline (Sigma-Aldrich), thereby preparing a 0.1 w/v % Tween 80-containing PBS (hereinafter called the test solution). The thickness of the matrix material was measured according with a digital indicator (U30A, manufactured by Sony Corporation). Matrix materials 1 to 3 (all manufactured by Japan Vilene Company, Inc.) shown in Table 1 were formed into 10 mm×10 mm squares, thereby preparing samples. The prepared samples were weighed, thereby obtaining their dry weights (hereinafter called weight A). Next, the foregoing samples were immersed in the test solution and fully impregnated with the test solution. The samples impregnated with the solution were slowly pulled out from the test solution (approximately 5 seconds/cm) and weighed, thereby obtaining their weight after test solution impregnation (hereinafter called weight B). Note that in the case where the matrix material has a film surface, it is weighed after the test solution adhered to the film surface after being pulled out has been wiped off, thereby obtaining weight B. Note that the thickness of the matrix material, weight A. and weight B were each measured three times, and the average values were adopted as the final values. The results are shown in table 1.

TABLE 1

| Matrix Material | Product Number | Base Material | Weight (g/m$^2$) | Thickness (μm) | Property | Water Holding Capacity (mg/cm$^2$) |
|---|---|---|---|---|---|---|
| 1 | EH-1212 | PET film/PET non-woven fabric | 12 | 38 | Hydrophilic | 4 |
| 2 | EW-0450 | PET film/PET non-woven fabric | 50 | 336 | Hydrophilic | 30 |
| 3 | EW-2080S | Polyester non-woven fabric | 80 | 600 | Hydrophobic | 55 |

In Vitro Flux Test

Human skin with an epidermis and stratum corneum was used to perform the in vitro flux test to study the possibility of controlling the drug release rate when matrix materials 1 to 3 are used in a patch.

Drug Patch Preparation

A punching die was used to form a backing layer material into a 25 mm×25 mm square. Next, a punching die was used to form matrix materials 1 to 3 each into 10 mm×10 mm squares. The formed matrix materials 1 to 3 were affixed to the center part of a backing layer material (hereinafter called blank patches 1 and 2). 0.1 w/v % Tween 80-containing water was added to a tube containing weighed methylnaltrexone bromide, thereby preparing a drug solution. A mechanical pipette was used to drip the desired drug solution onto the matrix material area of the blank patches 1 to 3. They were dried in a 50° C. oven for 15 minutes, thereby obtaining patch structures 1 and 2. A release liner was coated on the patch structures 1 and 2, then drug patches 1 and 2 were obtained. The completed patches were made into pouches together with a drying agent by sealing with a heat sealer.

Poration of Human Skin and Application of Patches

Human skin stored at −80° C. was left at room temperature for one hour, and after it had defrosted it was cut into a 3 cm×3 cm sizes, then used. A PBS was used as a receptor solution. Untreated human skin or human skin that had undergone poration treatment as desired were placed on cells. The perforated area of the human skin that had undergone poration treatment was 1 cm². Drug patches 1 to 3 were applied to the human skin. Fluid continued to be stirred, and the cells were kept at 32° C. At a desired observation time, 500 µl of the receptor solution was collected for analysis. Of the collected receptor solutions, 200 µl were analyzed by HPLC. The results are shown in FIG. 1. From FIG. 1, it is understood that drug patch 1 provided with matrix material 1 is anticipated to be able to be used more suitably for immediate release applications of drugs in comparison to drug patch 2 provided with matrix material 2 and drug patch 3 provided with matrix material 3.

Example 1

Drug Patch Preparation

A punching die was used to form a backing layer material (Polyethylene medical tape, 1774W, manufactured by 3M Company) into 25 mm×25 mm. Next, a punching die was used to form matrix material 1 into 10 mm×10 mm. The formed matrix material 1 was affixed to the center part of a backing layer material (hereinafter called a blank patch). 2 mg of measured zolmitriptan (molecular weight 287.36 (g/mol)) as API, 0.5 mg of sucrose and 4.0 mg of ascorbic acid that had been measured were placed in a tube as additives, dissolved in water, thereby preparing a drug solution. A mechanical pipette was used to drip the desired drug solution onto the matrix material area of the blank patches. They were dried in a 60° C. oven for 20 minutes, then patch structures were obtained. A release liner (silicone coated release liner, manufactured by Fujimori Kogyo Co., Ltd.) was coated on the patch structures, thereby obtaining drug patches. The completed patches together were made into pouches with a drying agent.

Animal Experiment: Transdermal Delivery by Microporation 77 to 84 day old hairless rats were used as experimental animals. A drug patch was affixed on the flank side of skin of experimental animals that had undergone poration treatment under the desired conditions. During the period where the patch was affixed, and after it had adhered, blood was collected at a desired time, each medicinal component was extracted according to a conventional method, then blood concentration was quantified by high performance liquid chromatography (LC-MS/MS).

Reference Example 1

Animal Experiment: Intravenous Administration 77 to 84 day old hairless rats were used as experimental animals. After intravenous administration of an drug solution (200 µl) containing 1 mg of zolmitriptan and 1 mg ascorbic acid, blood was collected at a desired time, each medicinal component was extracted according to a conventional method, then blood concentration was quantified by high performance liquid chromatography (LC-MS/MS).

Reference Example 2

Figure 2:
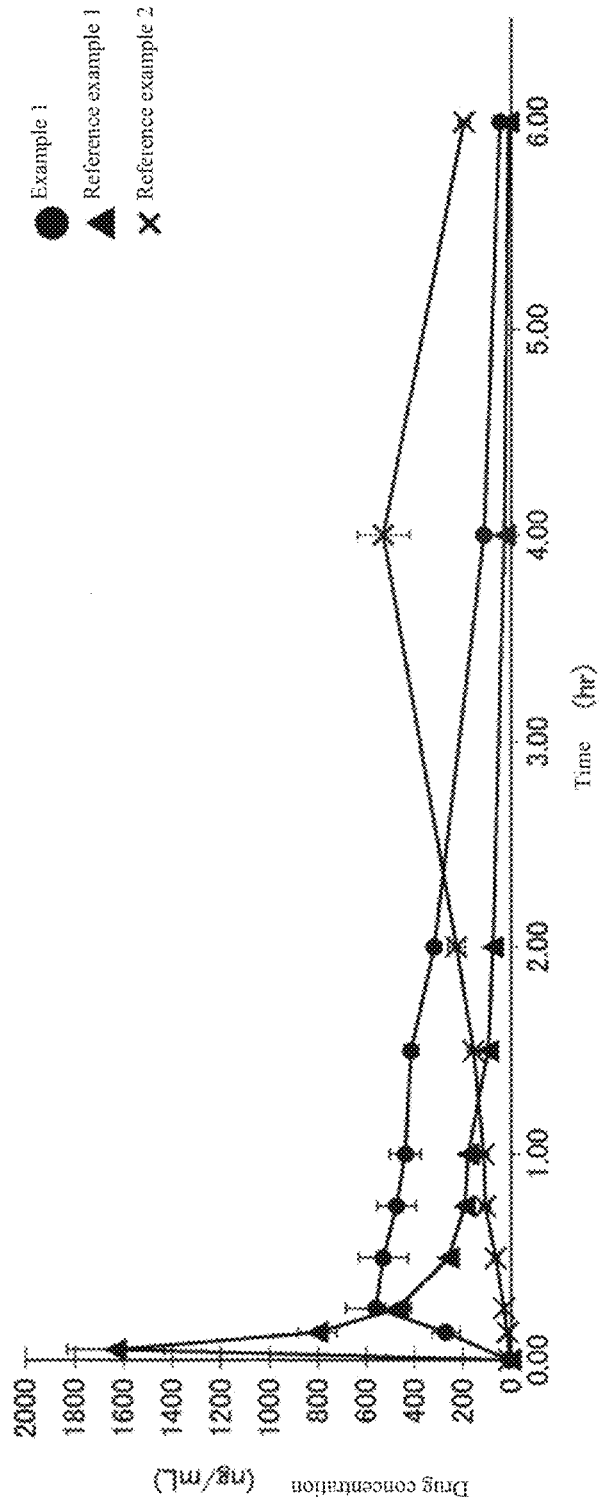
FIG. 2 is a drawing illustrating temporal changes in blood drug concentration obtained in Reference Example 1 and Reference Example 2.

Animal Experiment: Oral Administration 77 to 84 day old hairless rats were used as experimental animals. After oral administration of an drug solution (2.0 ml) containing 10 mg of zolmitriptan, 7.3 mg of citric acid, and 4.9 mg of sodium phosphate dibasic, blood was collected at a desired time, each medicinal component was extracted according to a conventional method, then blood concentration was quantified by high performance liquid chromatography (LC-MS/MS). The results obtained for example 1, reference example 1 and reference example 2 are shown in FIG. 2. From the results shown in FIG. 2, it is understood that the patch of example 1 can be used for immediate release applications of drugs that can be an alternative means of intravenous administration (reference example 1), and is much faster than that of reference example 2 (oral administration).

Example 2 and Comparative Example 1

Figure 3:
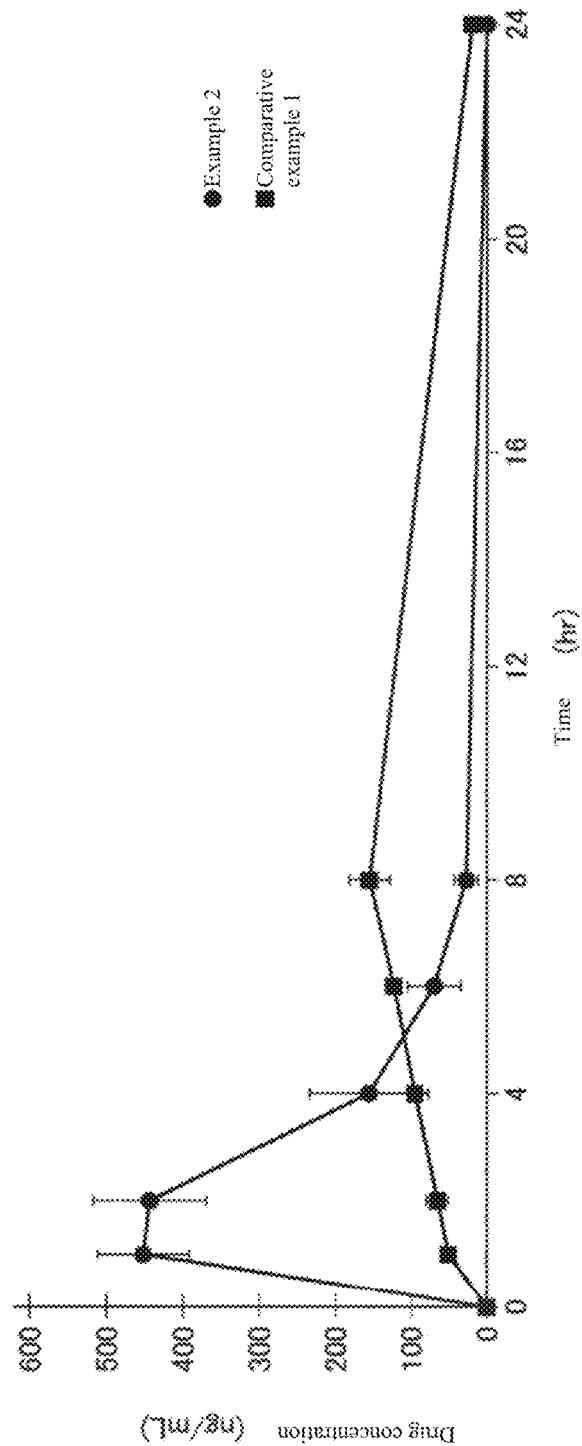
FIG. 3 is a drawing illustrating temporal changes in blood drug concentration obtained in Example 2 and Comparative Example 1.

A drug patch was prepared using the same method as example 1, with the exception that 5 mg of methyl naltrexone bromide (molecular weight 436.36 (g/mol)) was used as the drug, and transdermal delivery by microporation (example 2) using hairless guinea pigs as experimental animals was evaluated. Similarly, a drug patch was prepared in the same way as example 2, with the exception that matrix material 2 was used in place of matrix material 1, and transdermal delivery by microporation was evaluated (comparative example 1). The results obtained for example 2 and comparative example 1 are shown in FIG. 3. From the results shown in FIG. 3, it is understood that the patch of example 2 is different to the patch of comparative example 1, and it may be suitably used for immediate release applications of drugs.

Example 3 and Comparative Example 2

Figure 4:
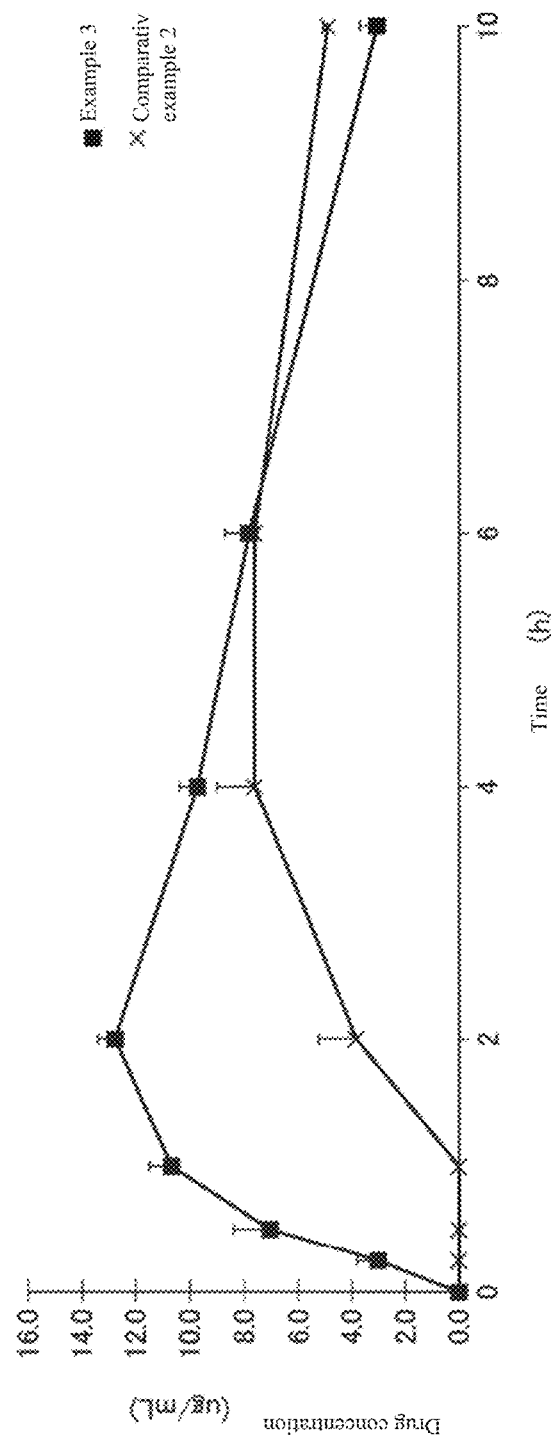
FIG. 4 is a drawing illustrating temporal changes in blood drug concentration obtained in Example 3 and Comparative Example 2.

A drug patch was prepared using the same method as example 1, with the exception that 6 mg of fondaparinux (molecular weight 1728 (g/mol)) was used as the drug, and transdermal delivery by microporation (example 3) was evaluated using hairless guinea pigs as experimental animals. Similarly, a drug patch was prepared using the same method as example 3, with the exception that matrix material 2 was used in place of matrix material 1, and transdermal delivery by microporation was evaluated (comparative example 2) using hairless guinea pigs as experimental animals. The results obtained for example 3 and comparative example 2 are shown in FIG. 4. From the results shown in FIG. 4, it is understood that the patch of example 3 is different to the patch of comparative example 2, and it may be suitably used for immediate release applications of drugs.

Example 4 and Comparative Example 3

Figure 5:
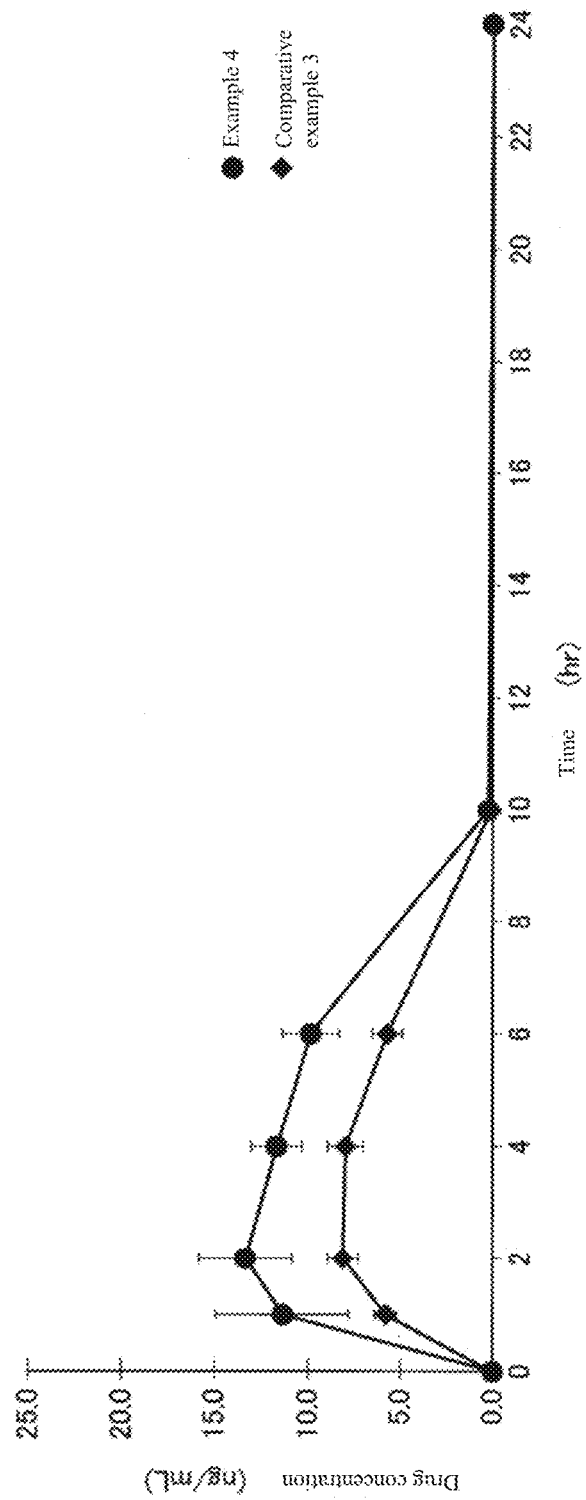
FIG. 5 is a drawing illustrating temporal changes in blood drug concentration obtained in Example 4 and Comparative Example 3.

A drug patch was prepared using the same method as example 1, with the exception that 0.1 mg of exenatide (molecular weight 4186.6 (g/mol)), and transdermal delivery by microporation was evaluated (example 4) using hairless guinea pigs as experimental animals. Similarly, a drug patch was prepared using the same method as example 4, with the exception that matrix material 3 was used in place of matrix material 1, and transdermal delivery by microporation was evaluated (comparative example 3) using hairless guinea pigs as experimental animals. The results obtained for example 4 and comparative example 3 are shown in FIG. 5. From the results shown in FIG. 5, it has been determined that the patch of example 4 is different to the patch of comparative example 3, in which the drug concentration reached maximum about 2.2 hours after the start of the measurement, and about 3.2 hours had elapsed until the drug concentration reached maximum, and it may be suitably used for immediate release applications of drugs.

dose study, AUCt (AUC (area under the blood concentration-time curve) up to a final sampling time t) and Cmax (maximum blood concentration) are used as bioequivalence determination parameters. If F (relative absorption of a test preparation relative to a standard preparation (aqueous solution or intravenous administration)) can be calculated by deconvolution, F can be used instead of AUC. Furthermore, AUC ∞ (AUC up to an infinite time), tmax (time to reach maximum blood concentration or time to reach maximum urinary excretion rate), MRT (mean retention time), and kel (disappearance rate constant) or the like are used as reference parameters. When urine is taken as bodily fluid, Aet (cumulative urinary excretion up to a final sampling time t), Aeτ (cumulative urinary excretion within one dosing interval (τ) after reaching steady state), Ae∞ (cumulative urinary excretion up to an infinite time), Umax (maximum urinary excretion rate), and Uτ (urinary excretion rate at τ time after administration in steady state) are used as parameters instead of AUCt, AUCτ (AUC within one dosing interval (τ) after reaching steady state), AUC∞. Cmax, and Cτ (blood concentration at t time after administration in steady state).

Furthermore, in "Bioequivalence Testing Guidelines for Generic Medicines of Topical Dermatological Prepara-

TABLE 2

| Experiment No. | Administered Drug | MW (g/mol) | Dose | Patch Composition Matrix Material | Additive | Experiment Animal | Administration Method |
|---|---|---|---|---|---|---|---|
| Example 1 | Zolmitriptan | 287.36 | 2 mg | 1 | Sucrose 0.5 mg Ascorbic acid 4.1 mg | Hairless Rat | Transdermal delivery |
| Reference Example 1 | | | 1 mg | — | Ascorbic acid 1 mg/200 ul water | Hairless Rat | Intravenous injection |
| Reference Example 2 | | | 10 mg | — | Citric acid monohydrate 7.3 mg Sodium phosphate dibasic 4.9 mg/ 3 ml water | Hairless Rat | Oral administration (solution) |
| Example 2 | Methyl Naltrexone Bromide | 436.36 | 5 mg | 1 | Sucrose 5 mg Tween 80 | Hairless Guinea Pig | Transdermal delivery |
| Comparative Example 1 | | | 5 mg | 2 | Sucrose 5 mg Tween 80 | Hairless Guinea Pig | Transdermal delivery |
| Example 3 | Fondapariunx | 1728 | 6 mg | 1 | None | Hairless Guinea Pig | Transdermal delivery |
| Comparative Example 2 | | | 6 mg | 2 | None | Hairless Guinea Pig | Transdermal delivery |
| Example 4 | Exenatide | 4186.6 | 0.1 mg (0.1 mg/cm2) | 1 | Sucrose 5 mg Tween 80 | Hairless Guinea Pig | Transdermal delivery |
| Comparative Example 3 | | | 0.1 mg (0.1 mg/cm2) | 3 | Sucrose 5 mg Tween 80 | Hairless Guinea Pig | Transdermal delivery |

The patch of the present invention includes a patch preparation for keeping the various drugs at a predetermined concentration or more, and a patch having the same bioavailability in bioequivalence tests. Here, a bioequivalence test refers to a test which determines a biological equivalent, that is, whether bioavailability (rate and amount of an unchanged substance or active metabolite entering the systemic circulation or rate and amount reaching the site of action) is equivalent, and specifically, it is possible to determine whether bioavailability is equivalent, according to bioequivalence tests described in, for example the "Guidelines for Bioequivalence Testing of Generic Drugs" and "Bioequivalence Testing Guidelines for Generic Medicines of Topical Dermatological Preparations" as determined by the Ministry of Health, Labor and Welfare of Japan, in PFSB/ELD Notification No. 1124005, dated Nov. 24, 2006 (Heisei 18).

For example, in "Guidelines for Bioequivalence Testing of Generic Drugs," in principle, when the crossover method is performed to collect blood as a bodily fluid, in the single tions," during the evaluation of bioequivalence of topical skin preparations, the most suitable test method can be selected according to the characteristics of drugs and preparations, such as 1. skin pharmacokinetic studies (equivalence assessment parameters: drug recovery at steady state, mean stratum corneum drug concentration or stratum corneum drug concentration), 2. pharmacological study (equivalence evaluation parameter: AUEC (area under the intensity-time curve of changing to a bluish tinge after removal of a preparation)), 3. residual amount test (equivalence evaluation parameter: amount of drug distributed from a preparation to the skin), 4. pharmacokinetic study (equivalence assessment parameter: blood concentration at AUC or steady state), 5. clinical trial (using clinical effect as an index), 6. in vitro efficacy testing (using in vitro efficacy as an indicator), and 7. animal test (the pharmacologic reaction that occurs on the skin surface of an animal by applying the preparation is used as an index).

Each of the foregoing test methods are selected as appropriate, the bioequivalence determination parameters for an obtained test preparation and standard preparation undergo statistics processing, and it is possible to determine whether the test preparation and standard preparation are biologically equivalent when within a predetermined range, yet, for example, in the "Guidelines for Bioequivalence Testing of Generic Drugs," when AUC and Cmax are lognormally distributed, the bioequivalent tolerance range is 0.80 to 1.25 when expressed as the ratio of the mean of the test preparation and standard preparation parameters, and when a 90% confidence interval of the mean value of the logarithm of the bioequivalence determination parameters of the test preparation and the standard preparation is in the range of log (0.80) to log (1.25), the test preparation and standard preparation are determined to be bioequivalent. Furthermore, in the "Bioequivalence Testing Guidelines for Generic Medicines of Topical Dermatological Preparations," when the equivalence assessment parameters can be regarded as log-normal distribution, the tolerance range of bioequivalence is represented by the ratio of the mean of the test preparation and standard preparation parameters, and is 0.80 to 1.25 for pharmaceuticals with a strong action, and 0.70 to 1.43 for pharmaceuticals other than those with a strong action, and when equivalence evaluation parameters are considered to be normally distributed, when the difference between the population mean of the test preparation and the standard preparation is expressed as a ratio to the population mean of the standard preparation, it is −0.20 to +0.20 for pharmaceuticals with a strong action and −0.30 to +0.30 for pharmaceuticals other than those with a strong action. When performing evaluations in efficacy tests or clinical tests, appropriate tolerance zones can be set according to the characteristics of the pharmaceutical. Note that the bioequivalence tests described in these guidelines are well known to those having ordinary skill in the art.

What is claimed is:

1. A transdermal drug delivery patch, comprising:
a matrix, and
at least one drug disposed within the matrix, wherein the matrix has a water holding capacity of 10 mg/cm$^2$ or less and a thickness of 100 μm or less, and the drug is a pharmaceutical having a molecular weight of 5000 or less, and the at least one drug is in an amount of 0.1 mg to 30 mg per cm$^2$ of the matrix.

2. The patch according to claim 1, wherein the matrix is a non-woven fabric.

3. The patch of claim 1, wherein the matrix has a weight of 100 g/m$^2$ or less measured in weight of the matrix per unit area of the matrix.

4. The patch of claim 1, wherein the pharmaceutical has a molecular weight of 2000 or less.

5. The patch of claim 1, wherein the pharmaceutical is a nonpeptide pharmaceutical.

6. The patch of claim 1, further comprising at least one hygroscopic agent disposed within the matrix.

7. The patch according to claim 6, wherein the hygroscopic agent is a saccharide.

8. The patch according to claim 6, wherein the total amount per unit area of the matrix with the drug and the hygroscopic agent disposed within the matrix is 0.1 to 30 mg/m$^2$.

9. The patch according to claim 8, wherein the total amount per unit area of the matrix with the drug and the hygroscopic agent is 0.1 to 20 mg/m$^2$.

10. The patch of claim 1, wherein the patch is configured to withdraw subcutaneous fluid of an amount of 9.5 to 85 mg/cm$^2$ per unit area of the matrix when applied to porated skin.

11. The patch of claim 1, further comprising at least one additive disposed within the matrix.

12. The patch of claim 1, further comprising a backing layer for supporting the matrix.

13. The patch of claim 1, used to deliver a drug transdermally through one or more micropores formed by a porator.

14. A system for delivering a drug through a target biological membrane, comprising:
a porator, and
a patch, wherein the patch comprises:
a matrix, and
at least one drug disposed within the matrix, wherein at least a portion of the drug is soluble in biological moisture received from the target through the micropores formed by the porator, the matrix has a water holding capacity of 10 mg/cm2 and a thickness of 100 μm or less, and the drug is a pharmaceutical having a molecular weight of 5000 or less, and the at least one drug is in an amount of 0.1 mg to 30 mg per cm$^2$ of the matrix.

15. The system according to claim 14, wherein the porator is at least one porator selected from a group composed of a heat porator, mechanical porator, laser porator, and water porator.

16. The system according to claim 14, wherein porator is a thermally conductive element disposed so as to be in substantial physical contact with a biological membrane to deliver sufficient energy to thermally ablate the biological membrane.

17. The system according to claim 14, wherein the porator is a thin layer tissue interface device.

18. The system according to claim 14, wherein the matrix is a non-woven fabric.

19. The system according to claim 14, wherein the matrix has a thickness of 100 μm or less.

20. The system according to claim 14, wherein the matrix has a weight of 100 g/m$^2$ or less measured in weight of the matrix per unit area of the matrix.

21. The system according to claim 14, wherein the pharmaceutical has a molecular weight of 2000 or less.

22. The system according to claim 14, wherein the pharmaceutical is a non-peptide pharmaceutical.

23. The system according to claim 14, wherein the patch further comprises at least one hygroscopic agent disposed within the matrix.

24. The system according to claim 23, wherein the hygroscopic agent is a saccharide.

25. The system according to claim 23, wherein the total amount per unit area of the matrix with the drug and the hygroscopic agent disposed within the matrix is 0.1 to 30 mg/cm$^2$.

26. The system according to claim 25, wherein the total amount per unit area of the matrix with the drug and the hygroscopic agent is 0.1 to 20 mg/cm$^2$.

27. The system according to claim 14, wherein the patch is configured to withdraw subcutaneous fluid of an amount of 9.5 to 85 mg/cm$^2$ per unit area of the matrix when applied to the target biological membrane.

28. The system according to claim 14, wherein the patch further comprises at least one additive disposed within the matrix.

29. The system according to claim 14, wherein the patch further comprises a backing layer for supporting the matrix.

30. A method for delivering a drug through a target biological membrane, comprising a step for forming one or more micropores on a biological membrane, and a step for placing a patch so as to be in physical contact with the one or more micropores, wherein the patch comprises:

a matrix, and at least one drug disposed within the matrix, wherein at least a portion of the drug is soluble in biological moisture received from the target through the one or more micropores, the matrix has a water holding capacity of 10 mg/cm2 or less and a thickness of 100 μm or less, and the drug is a pharmaceutical having a molecular weight of 5000 or less, and the at least one drug is in an amount of 0.1 mg to 30 mg per $cm^2$ of the matrix.

31. The method according to claim 30, wherein the one or more micropores are formed using a device selected from a group composed of a heat porator, mechanical porator, laser porator, and water porator.

32. The method according to claim 30, wherein one or more micropores are formed using a thermally conductive element disposed so as to be in substantial physical contact with a biological membrane to deliver sufficient energy to thermally ablate the biological membrane.

33. The method according to claim 30, wherein the one or more micropores are formed using a thin layer tissue interface device.

34. The method according to claim 30, wherein the matrix is a non-woven fabric.

35. The method according to claim 30, wherein the matrix has a weight of 100 $g/m^2$ or less measured in weight of the matrix per unit area of the matrix.

36. The method according to claim 30, wherein the pharmaceutical has a molecular weight of 2000 or less.

37. The method according to claim 30, wherein the pharmaceutical is a non-peptide pharmaceutical.

38. The method according to claim 30, wherein the patch further comprises at least one hygroscopic agent disposed within the matrix.

39. The method according to claim 38, wherein the hygroscopic agent is a saccharide.

40. The method according to claim 38, wherein the total amount per unit area of the matrix with the drug and the hygroscopic agent disposed within the matrix is 0.1 to 30 $mg/cm^2$.

41. The method according to claim 40, wherein the total amount per unit area of the matrix with the drug and the hygroscopic agent is 0.1 to 20 $mg/cm^2$.

42. The method according to claim 30, wherein the patch is configured to withdraw subcutaneous fluid of an amount of 9.5 to 85 $mg/cm^2$ per unit area of the matrix when applied to the target biological membrane.

43. The method according to claim 30, wherein the patch further comprises at least one additive disposed within the matrix.

44. The method according to claim 30, wherein the patch further comprises a backing layer for supporting the matrix.

* * * * *